(12) United States Patent
Bacastow

(10) Patent No.: US 11,129,606 B2
(45) Date of Patent: Sep. 28, 2021

(54) METHOD AND APPARATUS FOR INTERCONDYLAR NOTCH DISTRACTION KNEE ARTHROPLASTY

(71) Applicant: David Wesley Bacastow, Athens, GA (US)

(72) Inventor: David Wesley Bacastow, Athens, GA (US)

(*) Notice: Subject to any disclaimer, the term of this patent is extended or adjusted under 35 U.S.C. 154(b) by 107 days.

(21) Appl. No.: 16/873,067

(22) Filed: Jan. 27, 2020

(65) Prior Publication Data

US 2020/0297334 A1 Sep. 24, 2020

Related U.S. Application Data

(60) Provisional application No. 62/919,516, filed on Mar. 18, 2019.

(51) Int. Cl.
*A61B 17/02* (2006.01)
*A61F 2/38* (2006.01)

(52) U.S. Cl.
CPC .... *A61B 17/025* (2013.01); *A61B 2017/0268* (2013.01)

(58) Field of Classification Search
CPC ...... A61F 2/3859; A61F 2/389; A61F 2/3881; A61F 2/3877; A61F 2/3886; A61F 2/3854; A61F 2/30749; A61B 2017/0268; A61B 17/025
See application file for complete search history.

(56) References Cited

U.S. PATENT DOCUMENTS

2008/0167722 A1* 7/2008 Metzger .................. A61F 2/38
623/20.36

* cited by examiner

*Primary Examiner* — Samuel S Hanna

(57) ABSTRACT

A method and apparatus for distracting a joint during a procedure are disclosed. The apparatus can include bone engaging portions and an articulating bearing. The bone engaging portions can engage the bone and then the articulating portions can allow joint motion. The method can use the apparatus to perform a procedure with the apparatus.

2 Claims, 8 Drawing Sheets

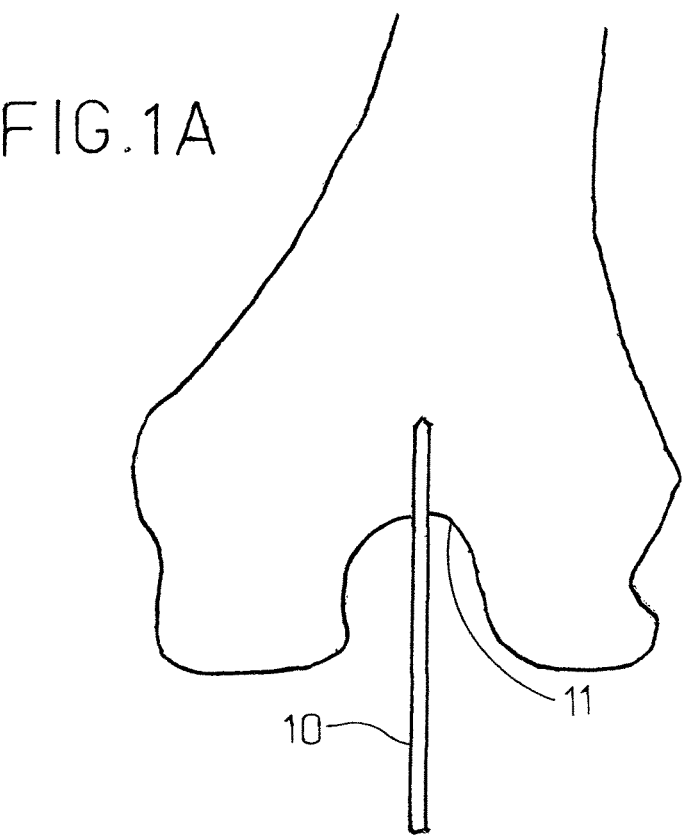

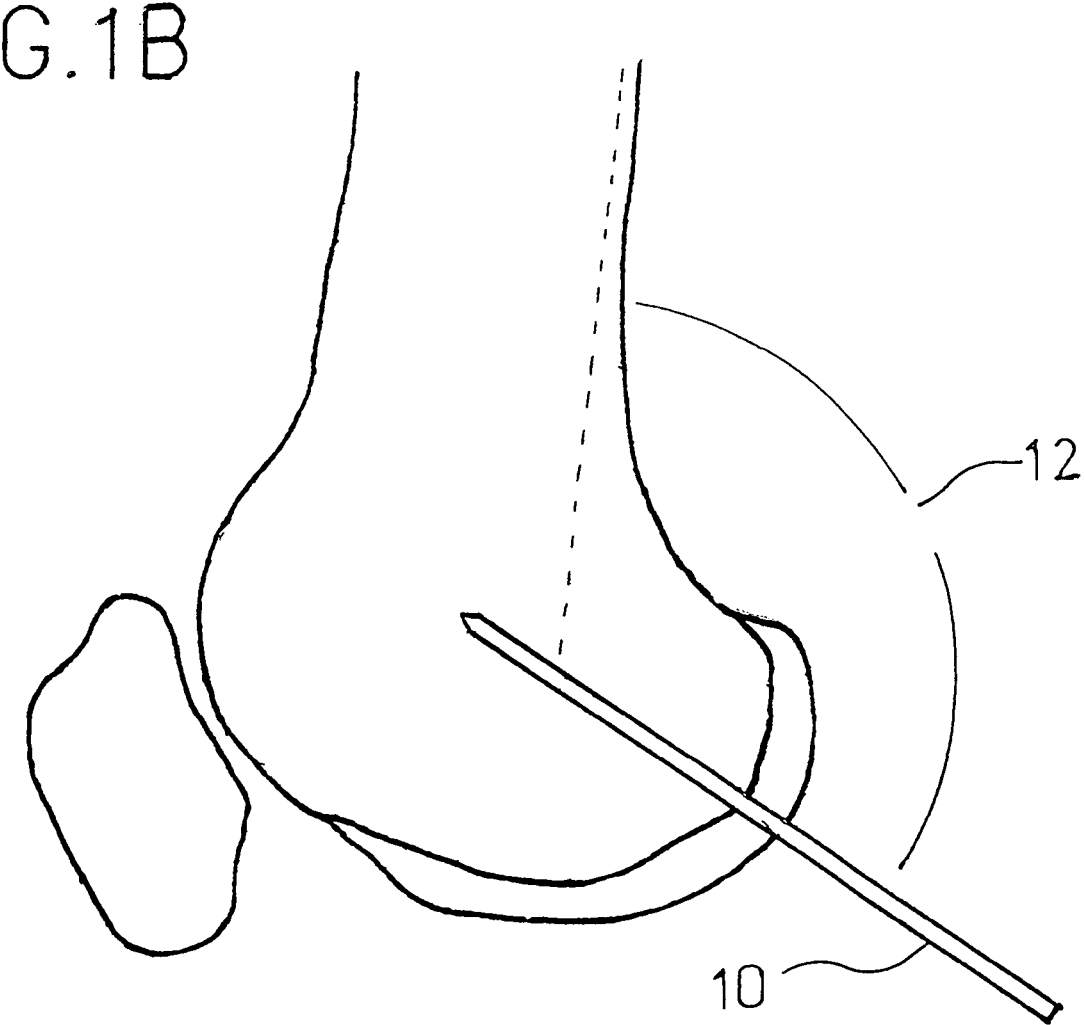

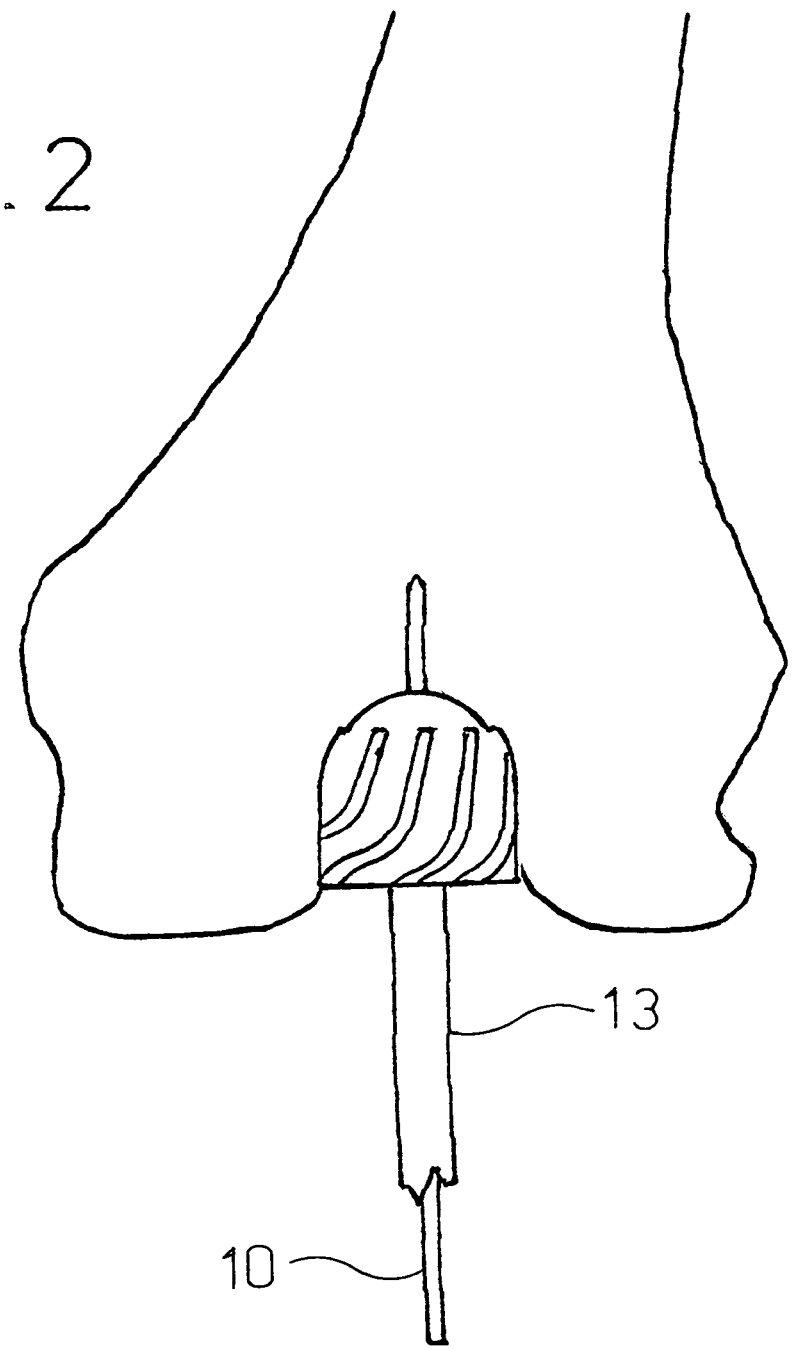

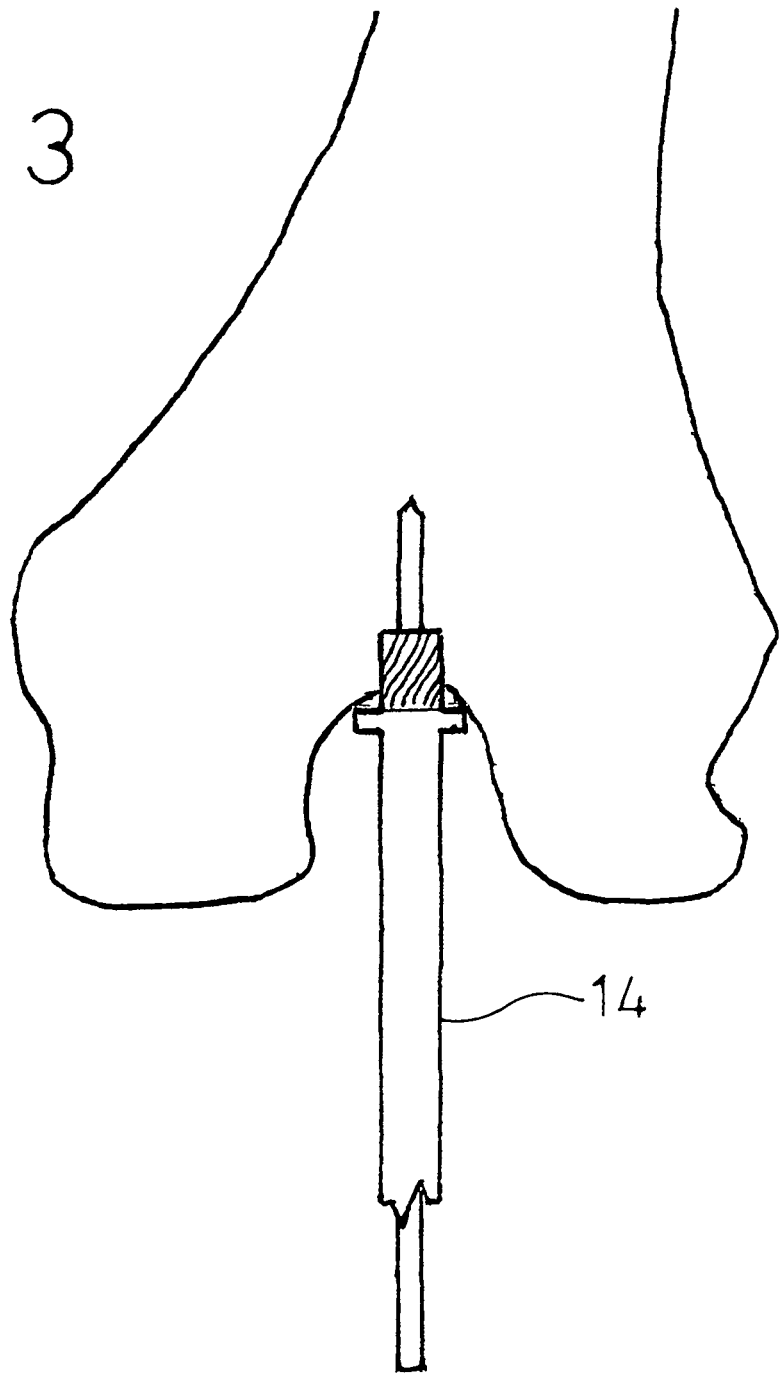

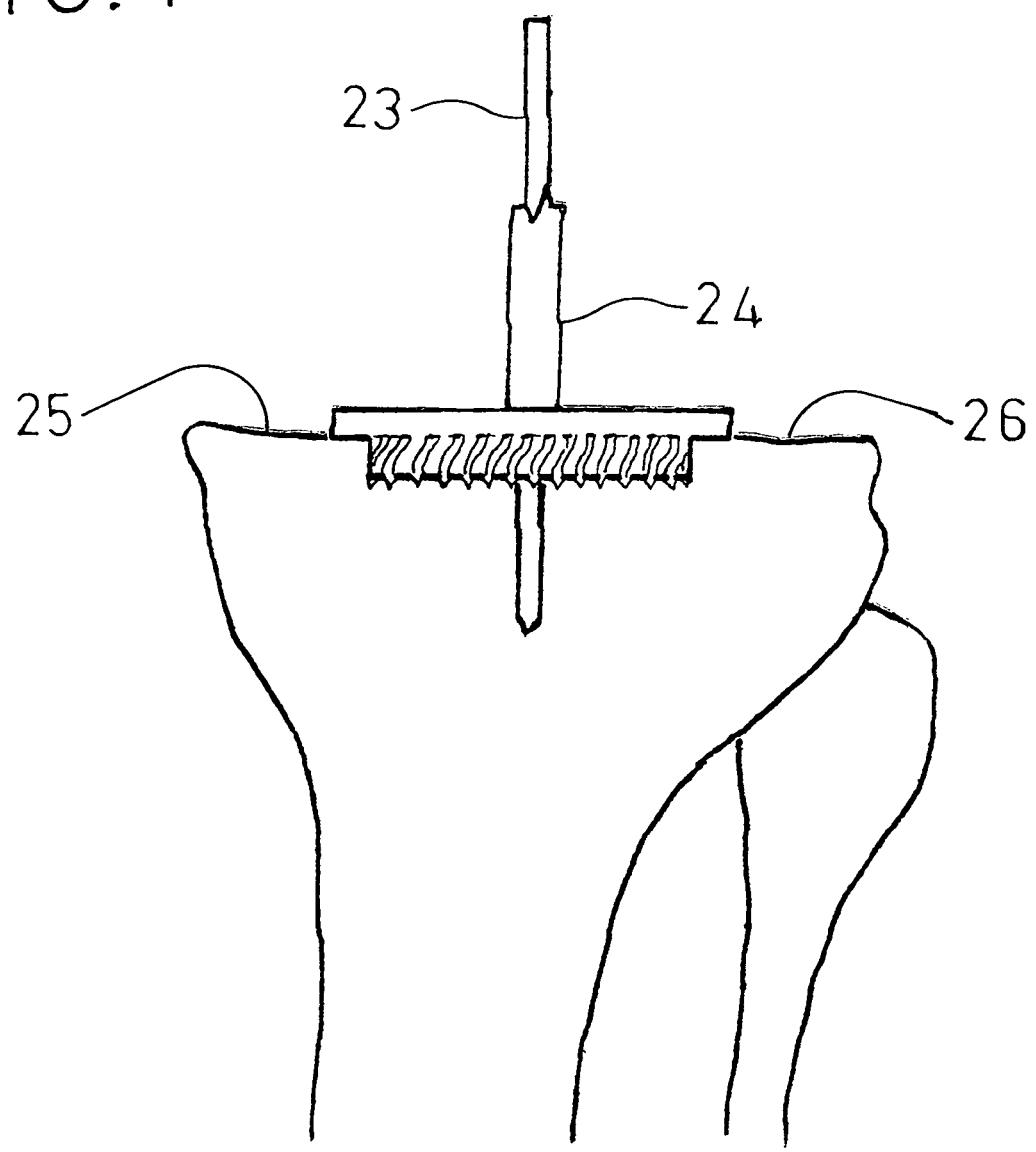

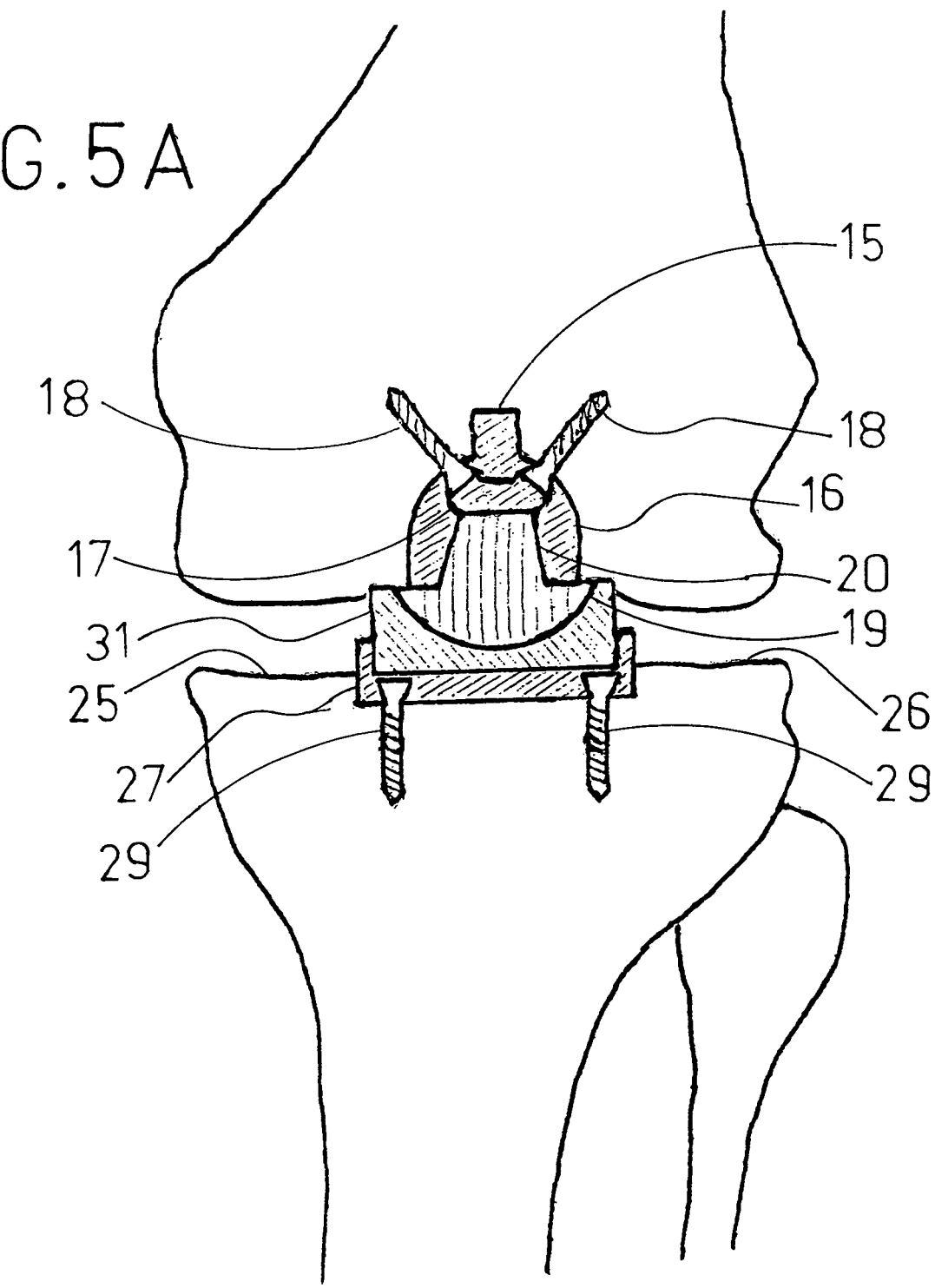

METHOD AND APPARATUS FOR INTERCONDYLAR NOTCH DISTRACTION KNEE ARTHROPLASTY

CROSS-REFERENCE TO RELATED APPLICATIONS

This application claims the benefit of U.S. Provisional Application No. 62/919,516, filed on Mar. 18, 2019. The disclosure of the above application is incorporated herein by reference.

COPYRIGHT NOTICE

A portion of the disclosure of this patent document may contain material which is subject to copyright protection. The copyright owner has no objection to the facsimile reproduction by anyone of the patent document or patent disclosure as it appears in the U.S. Patent and Trademark Office patent file or records, but otherwise reserves all copyright rights whatsoever.

FIELD

A method and device for distracting a joint during a procedure, in particular, a method and device for distracting a knee joint by placing an intercondylar bearing in a surgical procedure.

BACKGROUND

A knee joint may become damaged as a consequence of disease or injury, resulting in end stage arthritis and substantial or complete loss of the natural articulating cartilage surface. It may be selected to perform a procedure to restore the natural articulation.

For example, it is well known that articular cartilage, or hyaline cartilage has the ability to naturally repair or be replaced by fibrocartilage in a steroid free environment and in the presence of normal physiological joint motion with associated unloading of the joint contact pressure. This unloading generally might be accomplished with time limited options such as calibrated bicondylar distraction or articulated external fixation. In select patients it may be desirable to provide a method and apparatus for long term joint distraction.

SUMMARY

In contrast with total joint replacement, the method described and illustrated is a joint preserving procedure with placement of an axially aligned monoarticular bearing device which does not violate, alter or replace joint surfaces and requires only a minimally invasive limited incision approach. The method and apparatus taught herein may be used as a biological solution for arthritic disease in the knee joint. Generally, an incision can be made of the medial parapatellar type for joint access. The anterior and posterior cruciate ligaments must be surgically excised, with subsequent placement of an intercondylar distracting apparatus.

According to various embodiments, a distracting device for interconnection with a bone of an anatomy is disclosed. The device can include articulating femoral and tibial prosthetic bearing components.

According to various embodiments, a distracting device for interconnection with a bone of an anatomy is disclosed. The device can include a bone ingrowth portion to engage the femoral intercondylar notch. The device can also include a femoral bearing surface connected to the bone ingrowth portion by way of a morse taper.

According to various embodiments a distracting device for interconnection with a bone of an anatomy is disclosed. The device can include a bone ingrowth member to engage the proximal tibial surface. The device can also include a tibial bearing surface engaging the bone ingrowth portion with a tray and post mechanism or alternate assemblage design.

According to various embodiments a distracting device for interconnection with a bone of an anatomy is disclosed. The method can include femoral and tibia articulating portions to allow joint motion while distracting the preserved joint surfaces.

Further areas of applicability of the present teachings will become apparent from the detailed description provided herein after. It should be understood that the detailed description and various examples, while indicating the various embodiments, are intended for the purposes of illustration only and are not intended to limit the scope of the teachings.

BRIEF DESCRIPTION OF THE DRAWINGS

The present teachings will become more fully understood from the detailed description and accompanying drawings, wherein:

FIG. 1A is a femoral anatomical view from a coronal tunnel perspective demonstrating guide pin placement for femoral reaming.

FIG. 1B is a femoral anatomical view from a sagittal perspective showing guide pin placement for femoral reaming and referencing the posterior femoral shaft margin with an angle of 120 degrees.

FIG. 2 is a femoral anatomical view from a coronal tunnel perspective demonstrating reaming of the intercondylar notch.

FIG. 3 is a femoral anatomical view from a coronal tunnel perspective demonstrating drilling of the intercondylar notch dome for acceptance of a bone ingrowth post.

FIG. 4 is a tibial anatomical view from a coronal perspective showing reaming of the tibia over a guide pin for acceptance of a bone ingrowth tibial tray.

FIG. 5A is a detailed anatomical view of a knee joint illustrating an intercondyar notch distracting and bone interconnecting device engaging the femur and tibia according to the various embodiments.

DETAILED DESCRIPTION OF VARIOUS EMBODIMENTS

The following description of the various embodiments is merely exemplary in nature and is in no way intended to limit the teachings, their applications or uses. Other approaches to implementing the present invention and variations of the described embodiments may be constructed by a skilled practitioner and are considered within the scope of the present invention.

As opposed to total knee replacement or unicondylar knee replacement or patellofemoral knee replacement this design consists of an axially aligned intercondylar notch positioned monoarticular distracting bearing. A subset of patients with advanced end stage arthritis are not suitable candidates for a traditional total knee replacement due to their general medical condition, body habit or any number of other reasons. One group in particular that would benefit the most from the procedure described and illustrated includes those which are non-ambulatory or minimally ambulatory with fixed flexion contractors, where pain control is the primary consideration and the aim is to reduce or eliminate the need for use 4 of narcotic analgesics, a noteworthy goal in this group of typically elderly patients.

In this technique there is an element of distraction, not to the degree that might be obtained with calibrated bicondylar distraction or articulated external fixation but rather, that distraction which occurs as a result of dividing the anterior and posterior cruciate ligaments and resulting opening of particularly the flexion space where joint contact pressures are high especially in the context of a fixed flexion contracture. This minimal distraction is then maintained by placement of appropriately sized permanent components to partially unload the medial and lateral joint spaces. This unloading would not be expected to materially help pain symptoms due to disease in the patellofemoral compartment; removal of patellar osteophytes generally would be helpful in that regard.

To accomplish the procedure an anterior longitudinal medial parapatellar arthrotomy approach is made similar to that used for retrograde femoral or antegrade tibial intramedullary nailing. If patellar eversion is undertaken it must be done so with extreme caution so as to avoid damage to the extensor mechanism given the expected presence of a fixed flexion contracture. A patellar displacing approach would be preferred.

With reference to FIG. 1A, FIG. 1B and FIG. 2, after curetting away remnants of the divided cruciate ligaments a guide pin 10 is placed through the roof 11 of the intercondylar notch approximately at the center of the distal femur as monitored on biplanar fluoroscopy and referencing the posterior femoral shaft margin with an angle 12 of 120 degrees.

Figure 5B:
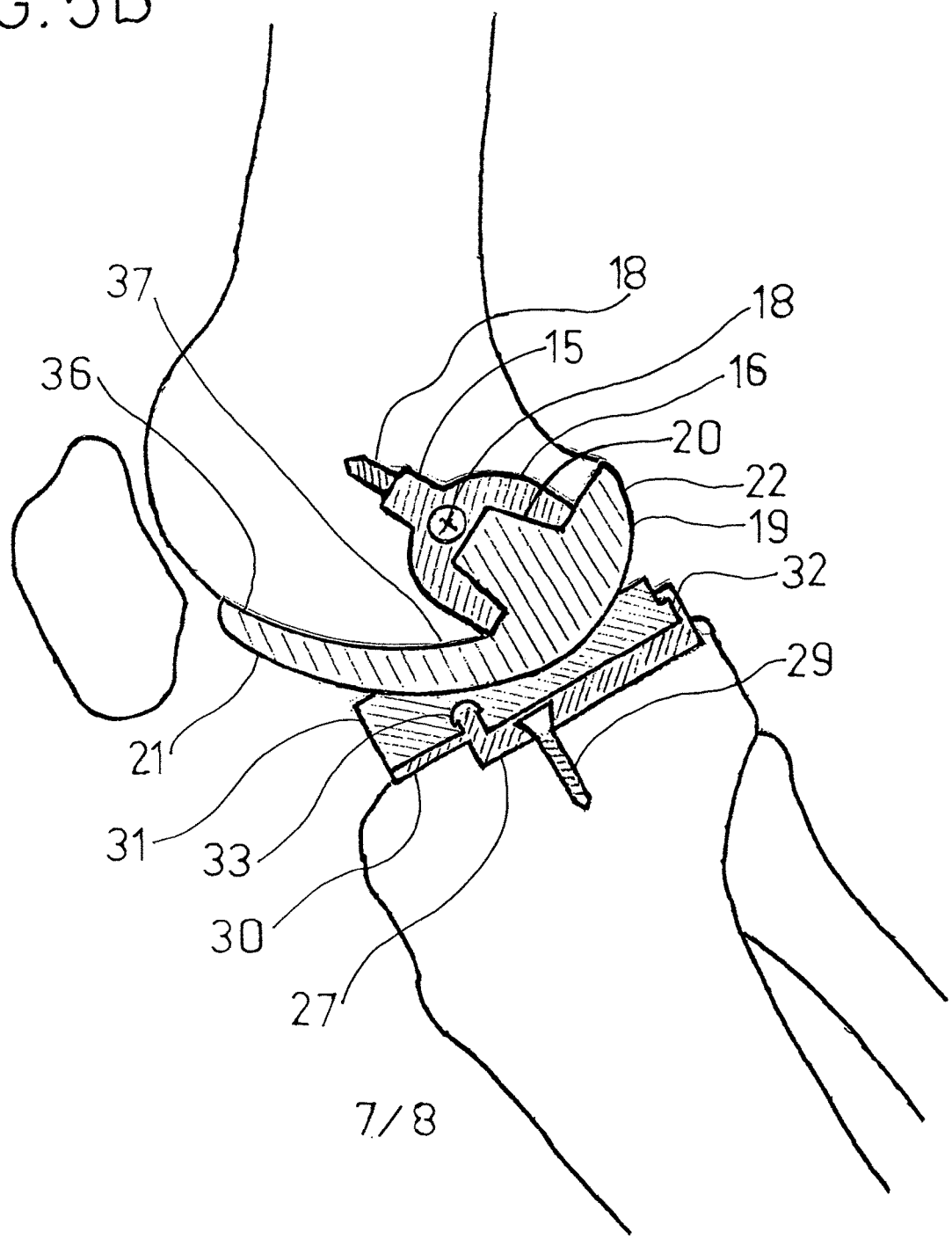
FIG. 5B is a detailed anatomical view of a knee joint illustrating an intercondylar notch distracting and bone interconnecting device engaging the femur and tibia according to various embodiments.

With reference to FIG. 2, the notch is then reamed with a cylindrical shaped blunt nosed side cutting reamer 13 so as to preserve the roof of the notch, which will then later, as shown in FIG. 3, be drilled 14 to a diameter of approximately 8 millimeters to accept, as can be seen in FIG. 5A and FIG. 5B, an integral axial post 15 with bone ingrowth surface treatment attached to the body 16 of the femoral component which also is cylindrical in shape ending proximally in a dome, with a range of approximately 20 to 25 millimeters in diameter, also with a bone ingrowth surface, and similar length options to accommodate variability in the size and shape of the adult human femur. The goal is to ream the center 65 to 75 percent of the notch for engagement of the femoral component with cancellous bone while maintaining the cortical margins of the notch. The body 16 of the femoral bone ingrowth component, made of titanium or tantalum or other material with a surface texture conducive to bone ingrowth, will be cylindrical in cross section with a superior dome and integration post 15 and a central concavity 17 to accept diagonally placed fixation screws 18. The femoral bone ingrowth component 16 could be made an alternate shape to accommodate the notch anatomy, including a customized fit specific to a particular patient based on pre-operative CT or other cross-sectional imaging.

Again referencing FIG. 5A and FIG. 5B, which illustrate, according to various embodiments, an apparatus for intercondylar notch distraction knee arthroplasty, a modular ferrous metal bearing 19 will attach to the femoral bone ingrowth component 16 by way of a morse taper 20. A ceramic bearing would be another option especially in patients with a specific metal allergy as could titanium even with the anticipated wear characteristics of the later in this group of low demand patients. The shape of the modular femoral bearing surface 19 on coronal section will be a spherical cap while that in the sagittal plane closely follows the normal anatomy of the adult human femur with that of an ellipse, and more particularly an oblate spheroid anteriorly 21, merging to that of a spherical cap posteriorly 22. The modular femoral bearing 19 will have variable thickness and diameter sizing options for optimal distraction and stability.

With reference to FIG. 4, the tibial surface will be initially prepared removing the divided anterior and posterior cruciate ligament remnants and tibial spines with a ronguer and then placing an axially aligned centrally located guide pin 23 over which will be used a cannulated Forstner type reamer 24 to a depth of 3 to 5 millimeters below the adjacent medial 25 and lateral 26 tibial plateaus. The diameter of the reamer may vary depending on the bone quality to determine which size tibial bone ingrowth tray 27 would be most appropriate.

Figure 6:
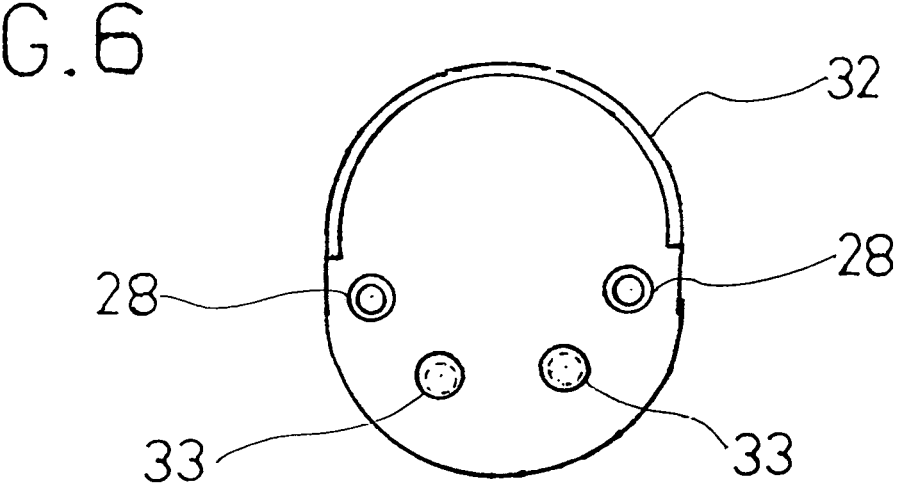
FIG. 6 is a top view of a tibial bone ingrowth tray according to various embodiments.

With reference to FIG. 6, the tibial bone ingrowth tray 27 will be stabilized with two or more fixation screws 29, utilizing integral fixation holes 28, and possibly also a centrally placed supplemental modular stabilization stem.

The tibial bone ingrowth tray 27 will have an anterior lip 30, which extends beyond the circular shaped bone ingrowth surface. Except for the anterior lip, which rests on the tibial surface, the tibial tray 27 is inset within the proximal tibia to a depth of 3 to 5 millimeters below the adjacent medial 25 and lateral 26 tibial plateaus commensurate with the depth of reaming.

Figure 7:
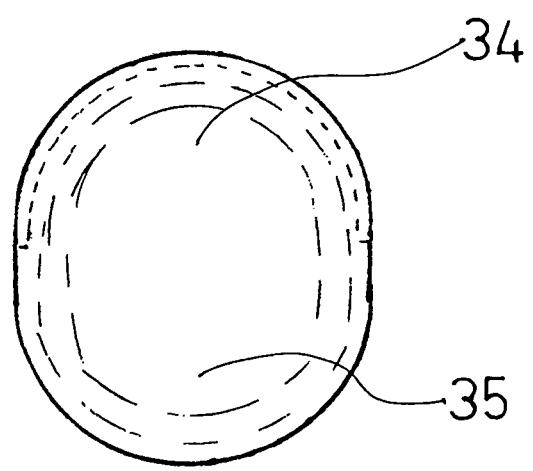
FIG. 7 is a top view of a tibial polyethylene bearing surface according to various embodiments.

With reference to FIG. 7, a high density polyethylene tibial bearing surface 31 with complementary size and shape to the chosen femoral bearing 19 will attach to the tibial tray 27 with an integral fixation design, utilizing a retaining lip 32 in the tray posteriorly and two posts 33 on the tray anteriorly for both fixation and rotational stability, utilizing trials before permanent sizing is determined. The tibial polyethylene bearing surface posteriorly 34 closely matches the shape of the femoral bearing 19 posteriorly 22 when engaged in flexion but widens anteriorly 35 by 2 millimeters where it engages the anterior 21 femoral bearing 19 with deepening of the anterior polyethylene articular surface 35 also by 2 millimeters while maintaining the same radius of curvature so as to mitigate any tendency for component dissociation in extension and to allow sliding motion for rotational positioning in extension, as a priority over polyethylene wear characteristics in this group of presumably relatively sedentary patients.

In addition to the morse taper 20 stability of the anterior bone engaging aspect 36 of the femoral bearing 22 is achieved by slightly insetting the component into the distal grooved surface of the femoral trochlea approximately 1 millimeter at the mid trochlea 36, increasing to approximately 3 millimeters posteriorly 37 where it merges with the intercondylar notch, and possibly also incorporating a bone ingrowth surface.

As unloaded regenerating articular cartilage will respond better to a relatively bloodless environment, a temporary suction drain would be appropriate especially if there is an indication for patellar osteophyte removal. An initial bulky bandage possibly with a contoured supportive splint would be advised until the wound is stabilized followed by resumption of normal pre-operative bed to chair activities. Post-operative physical therapy is not recommended at least until component bone ingrowth has been demonstrated on follow-up radiographs.

What is claimed is:

1. A distracting device for interconnection with a femur and a tibia of a knee joint implemented as a knee prosthesis assembly comprising:
    a femoral engaging member comprising a body having an outer bone engaging surface defining a bone ingrowth surface and an opposite inner surface defining a conical cavity, wherein said femoral engaging member is shaped to be inserted into the intercondylar notch;
    a bone attachment mechanism comprising at least two bone fixation screws extending from the femoral engaging member configured for securing the femoral engaging member into the intercondylar notch until bone ingrowth occurs between the femoral engaging member and the femur;
    a femoral bearing portion comprising a conical post to be received into the conical cavity of the femoral engaging member by way of a morse taper and an opposite articulating surface extending between condyles of the femur without involving the condyles of the femur;
    a tibial engaging member comprising a tibial tray having a bone engaging surface defining a bone ingrowth surface and an opposite inner surface defined by an upstanding retaining lip extending around a posterior margin of the tibial tray and including two upstanding posts;
    a bone attachment mechanism comprising at least two bone fixation screws extending from the tibial engaging member configured for securing the tibial engaging member to the tibia until bone ingrowth occurs between the tibial engaging member and the tibia; and
    a tibial bearing section attached to the tibial engaging member by the retaining lip and the posts, said tibial bearing section comprises an articulating surface;
    wherein the articulating surface of the femoral bearing portion configured to articulate relative the articulating surface of the tibial bearing portion to thereby articulate the femur relative to the tibia,
    wherein insertion of the distraction device into the knee joint configured to distract the condyles of the femur away from plateaus of the tibia.

2. A method for distracting a knee joint with the distracting device of claim 1, the method comprising:
    Reaming an intercondylar notch of a femur and a tibial of the knee joint;
    Placing and securing the femoral engaging member of the distracting device of claim 1 into the reamed concavity of the intercondylar notch;
    Placing and securing the tibial engaging member of the distracting device of claim 1 into the reamed surface of the tibia;
    Coupling the femoral bearing portion of the distracting device of claim to 1 to the femoral engaging member;
    Coupling the tibial bearing section of the distracting device of claim to 1 to the tibial engaging member; and
    Contacting the femoral bearing portion with the tibial bearing section to allow relative articulation between the femur and the tibia of the knee joint while being distracted away from one another.

\* \* \* \* \*